(12) United States Patent
Raisanen

(10) Patent No.: US 7,216,417 B2
(45) Date of Patent: May 15, 2007

(54) METHOD FOR MANUFACTURING AN ELECTROMECHANICAL SENSOR ELEMENT

(75) Inventor: Heikki Raisanen, Jyvaskyla (FI)

(73) Assignee: Emfitech Oy, Jyvaskyle (FI)

( * ) Notice: Subject to any disclaimer, the term of this patent is extended or adjusted under 35 U.S.C. 154(b) by 837 days.

(21) Appl. No.: 10/267,554

(22) Filed: Oct. 4, 2002

(65) Prior Publication Data

US 2003/0073936 A1    Apr. 17, 2003

Related U.S. Application Data

(63) Continuation of application No. PCT/FI01/00333, filed on Apr. 5, 2001.

(30) Foreign Application Priority Data

Apr. 6, 2000 (FI) .................................. 20000811
Jan. 2, 2001 (FI) .................................. 20010004

(51) Int. Cl.
*G01R 3/00* (2006.01)
(52) U.S. Cl. .......................... 29/595; 29/417; 29/592.1; 29/609; 29/846; 156/73.1; 156/164; 156/229; 156/273; 156/322; 156/324; 216/22; 216/39; 216/41; 310/311; 310/314; 310/317; 310/344; 381/114; 381/116; 381/191; 427/79; 427/80
(58) Field of Classification Search .................. 29/417, 29/592.1, 595, 609, 831, 846; 156/73.1, 156/164, 229, 273.1, 273.3, 273, 274.6, 308, 156/322, 324; 216/22, 39, 41, 4; 310/311, 310/314, 317, 344; 381/114, 116, 191; 427/79, 427/80

See application file for complete search history.

(56) References Cited

U.S. PATENT DOCUMENTS 3,943,614 A * 3/1976 Yoshikawa et al. ........ 29/25.35

(Continued)

FOREIGN PATENT DOCUMENTS

EP    0 775 049    12/1999

(Continued)

OTHER PUBLICATIONS

ETMF-Polymer Transducer as a Detector of Respiration in Humans; Siivola, et al. Medical & Biological Engineering & Computing, Nov. 1993; pp. 634-635.

(Continued)

*Primary Examiner*—Paul D. Kim
(74) *Attorney, Agent, or Firm*—Katten Muchin Rosenman LLP

(57) ABSTRACT

Method for manufacturing an electromechanical sensor element for converting mechanical forces produced by the movements and vital functions or a person into electric signals, in which method a sensor film (11) is provided with metallic electrodes (15,16) placed on either side of it, at least one of said electrodes being a signal electrode, in which method is produced by cutting off a larger amount of sensor element material, in which method in the manufacture of sensor element material the electrodes are created in a continuous roll-to-roll process, and in which method the sensor element material is produced by laminating as a continuous roll-to-roll process. At least the sensor element material consists of repeated electrode patterns and a sensor element of a desired size and/or shape is formed by cutting the material between the patterns.

6 Claims, 7 Drawing Sheets

U.S. PATENT DOCUMENTS

Figure 1:
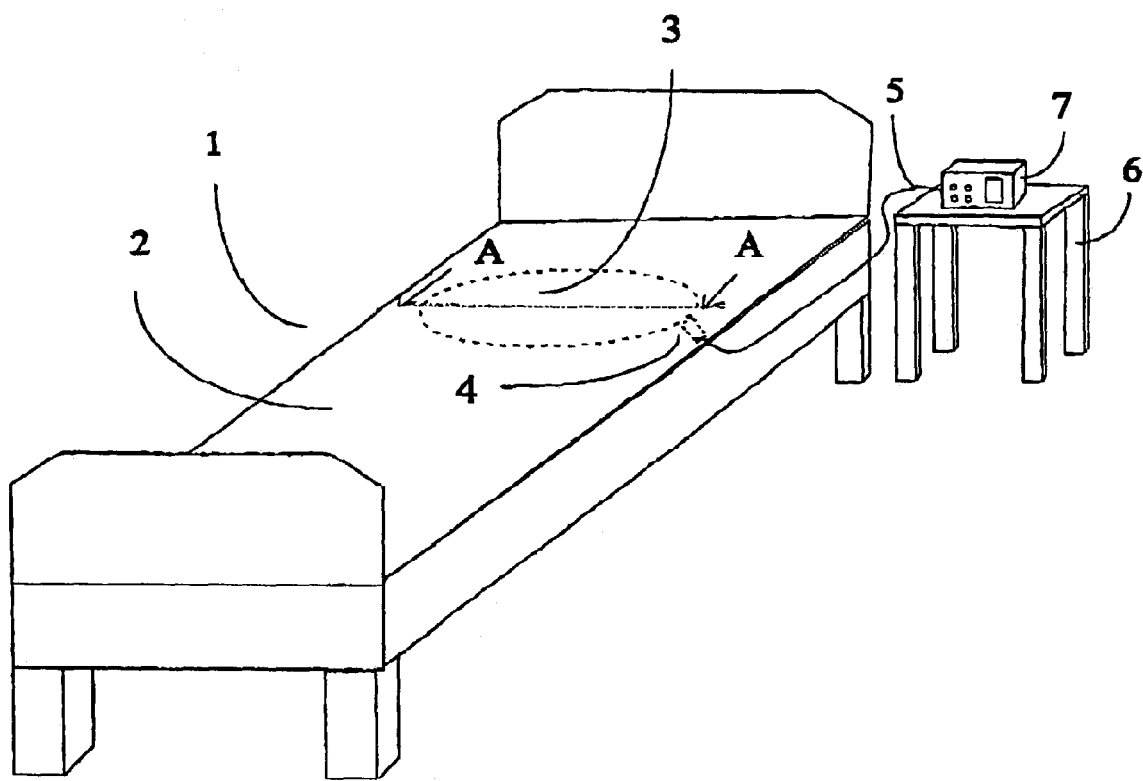

| | | | | |
|---|---|---|---|---|
| 4,370,182 A | * | 1/1983 | Becker et al. | 156/52 |
| 4,509,527 A | | 4/1985 | Fraden | |
| 4,654,546 A | * | 3/1987 | Kirjavainen | 307/400 |
| 4,874,659 A | | 10/1989 | Ando et al. | |
| 5,448,996 A | | 9/1995 | Bellin et al. | |
| 5,844,488 A | | 12/1998 | Musick | |
| 5,912,759 A | * | 6/1999 | Good et al. | 359/297 |
| 5,964,720 A | | 10/1999 | Pelz | |

FOREIGN PATENT DOCUMENTS

| | | |
|---|---|---|
| FI | 913741 | 2/1993 |
| GB | 2 069 238 | 8/1981 |
| WO | 96/05045 | 2/1996 |
| WO | 96/06718 | 3/1996 |
| WO | 98/52467 | 11/1998 |
| WO | 01/02823 | 1/2001 |

OTHER PUBLICATIONS

New Noninvasive Piezoelectric Transducer for Recording of Respiration, Heart Rate and Body Movements; Siivola, J. Medical & Biological Engineering & Computing, Jul. 1989; pp. 423-424.

* cited by examiner

METHOD FOR MANUFACTURING AN ELECTROMECHANICAL SENSOR ELEMENT

This application is a continuation of PCT/FI01/00333 filed on Apr. 5, 2001.

The present invention relates to a sensor system for monitoring the condition of a person on a planar support, said system comprising a planar sensor element fitted on the support for converting mechanical forces produced by the person's movements and vital functions into electric signals, and an interface for the connection of the sensor via a connection cable to a monitoring unit. The invention also concerns a method for manufacturing the sensor system.

Previously known is a so-called electret field, i.e. a permanent electric charge injected into a dielectric material by ionization. A film applicable as a sensor film of a sensor element according to the invention is presented in U.S. Pat. No. 4,654,546, in which a dielectric plastic film containing flat or ripped gas blisters is used to form a so-called electret bubble film. Both surfaces of the film are metal-coated. WO specification 96/06718 presents a procedure for expanding a thin foamed plastic film, in which procedure the amount of gas contained in it can be more than doubled. EP patent specification EP-B1-0775049 describes how a thin biaxially oriented film containing flat gas blisters is electrically charged so that partial discharges occur in the gas blisters inside it. Patent specification FI 913741 presents various electric structures for sensor elements. Previously known are also fibrous polarized electret films, as presented e.g. in U.S. Pat. No. 4,874,659. Likewise, piezo-electric sensor films, such as PVDF, are known and they are also applicable for use in the sensor element of the invention.

U.S. Pat. No. 5,448,996 presents a planar sensor system for the monitoring of a patient's condition, such as respiration, heart beat, and body movements, which uses orthogonal sensor element sheets containing longitudinal piezo-electric sensor strips, said sheets being placed in the patient's bed. Individual sensor strips may also be of a circular or square form. Another piezo-electric sensor is described in the article J. Siivola: "New noninvasive piezo-electric transducer for recording respiration, heart rate and body movements", Medical & Biological Engineering & Computing, July 1989, which presents a piezo-electric PVDF converter for converting the forces produced on the patient support by respiration, heart beats and body movements into electric signals. According to the article, the sensor has electrodes consisting of aluminum and chromium metal layers of a thickness of 30 nm on both sides of a PVDF polymer film. The connection leads are coupled to the electrodes using conductive epoxy glue.

The so-called electret field, i.e. a permanent electric charge injected into dielectric material by ionization, is based on ions being locked in molecules and the crystal structure. A film applicable for use as the active electromechanical material of a patient sensor is described in the article J. Siivola, K. Leinonen, L. Räisänen: "EMF-polymer transducer as a detector of respiration in humans", Medical & Biological Engineering & Computing, November 1993. This film consists of dielectric plastic film, such as polypropylene, containing flat or ripped gas blisters, constituting an electret film (so-called electret bubble film). Unlike the piezo-electric PVDF film, which is sensitive to bending, the electret bubble film containing flat gas blisters is very sensitive to variation of thickness. This provides an advantage in an application according to the invention. The raw material of the electret bubble film, typically polypropylene, involves no environmental hazard even when burning, unlike PVDF, which contains very toxic fluoride.

A specific disadvantage associated with prior-art sensor elements is a difficult and expensive manufacturing process. The object of the present invention is to eliminate the drawbacks of prior-art solutions and achieve a new type of sensor system whose manufacture produces no detrimental environmental stress and which contains no environmentally hazardous toxic substances, in which the sensor produces both an optimal respiration signal and an optimal heartbeat signal, and in which the manufacturing costs of the sensor element per unit have been minimized.

In a preferred embodiment of the invention, the sensor has a substantially oval shape, this solution being based on the observation that a patient generally lies in the middle region of a bed. Since a human being has a substantially oval shape in longitudinal cross-section, the weight distribution caused by the body diminishes toward the edges of the bed.

It has been established that using a narrow, eg about 5 cm wide and 60 cm long sensor strip based on electret bubble film, heartbeat is well registered, whereas respiration is not so clearly perceived. Likewise, we have discovered that, using a similarly manufactured sensor strip 50 cm wide and 60 cm long, respiration is clearly perceived while heartbeat is not so clearly detected. We have found that the best combination is a sensor about 30 cm wide and 60 cm long and having a rectangular or preferably oval form. Such a sensor is capable of clearly distinguishing both respiration, including snoring, and heartbeat.

An embodiment of the invention in which an aluminum/polyester film is used in the sensor element is additionally characterized in that the area of connection of the connecting cable is silvered e.g. by printing with silver pasta.

In the method of the invention, an electromechanical sensor film, such as an electret bubble film which has a permanent electric charge injected by ionization and which may also consist of a plurality of films glued together, is provided with film-like metallic electrodes placed on both of its outer surfaces, the outer surface of at least one of the metal electrodes being provided with a film-like insulating material, which may also consist of the same electromechanical sensor film.

The method of the invention for manufacturing a sensor system from a sensor element material is characterized in that at least the signal electrode material is provided with repeated electrode patterns. The sensor element is formed by cutting the sensor element material between electrode patterns.

In detail, the system and method of the invention are characterized by what is presented in the attached claims.

By applying the manufacturing technique of the invention, it is possible to produce sensors the size of a whole bed by cutting the sensor from sensor material manufactured as long continuous sheets divided into areas measuring e.g. about 30×60 cm.

By using a sensor element of a shape as provided by the invention and manufactured by the method of the invention, it will be possible to optimize the amount of material needed for the sensor element so that no material is wasted. Moreover, the sensor element of the invention is less susceptible to interference and damage than currently used sensor elements. In addition, the silvering used in the area of connection of the connecting cable minimizes damage that may arise at the joint as a result of bending and handling. Furthermore, using an electret bubble film, the sensor element can be made very thin and elastic.

By the method of the invention, sensor element material can be manufactured economically and fast by mass production in the form of material rolls, which cab be cut so as to produce reliable film-like sensor elements of desired length and width that are well protected against electromagnetic interference, to be used for monitoring the vital functions of patients. When the electrodes used are aluminum electrodes, which can be etched using iron chloride, the method of the invention is very advantageous and environmentally friendly.

A feature typical of a preferred embodiment of the invention is that in its manufacture the signal, earth and zero electrodes are produced by printing (e.g. using an ink jet printer) or by silk screen printing electrode patterns on the metal coat on the surface of the dielectric film using e.g. a dielectric insulating material that dries under UV light and etching away the areas outside the patterns. Both the printing, drying, etching and washing of the electrode pattern, all take place in a roll-to-roll process. Similarly, the gluing together or lamination of the electromechanical film is carried out in a roll-to-roll process.

A preferred embodiment of the invention is additionally characterized in that that the electret bubble film used is expanded before being charged, e.g. by the method presented in WO specification 96/06718, the amount of gas contained in it being thus increased to a level exceeding 50%. When the film is then charged, its sensitivity is increased by multiple times as compared with an unexpanded film. A feature typical of the process of charging the film by ionization is that it gives rise to partial discharges, as described in EP patent specification EP-B1-0775049. Furthermore, the invention using an electret bubble film is additionally charcaterized in that the sensor element has been heavily seasoned by keeping it at a temperature somewhat above the desired maximum operating temperature, e.g. at 60° C., for several days. This reduces the sensitivity of the sensor by about 20–25% as compared with the original situation. As a result, the sensor becomes very stable in respect of temperature variations.

Figure 2A:
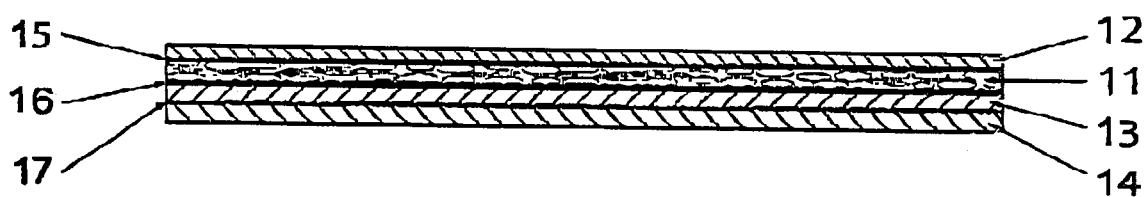
Figure 2B:
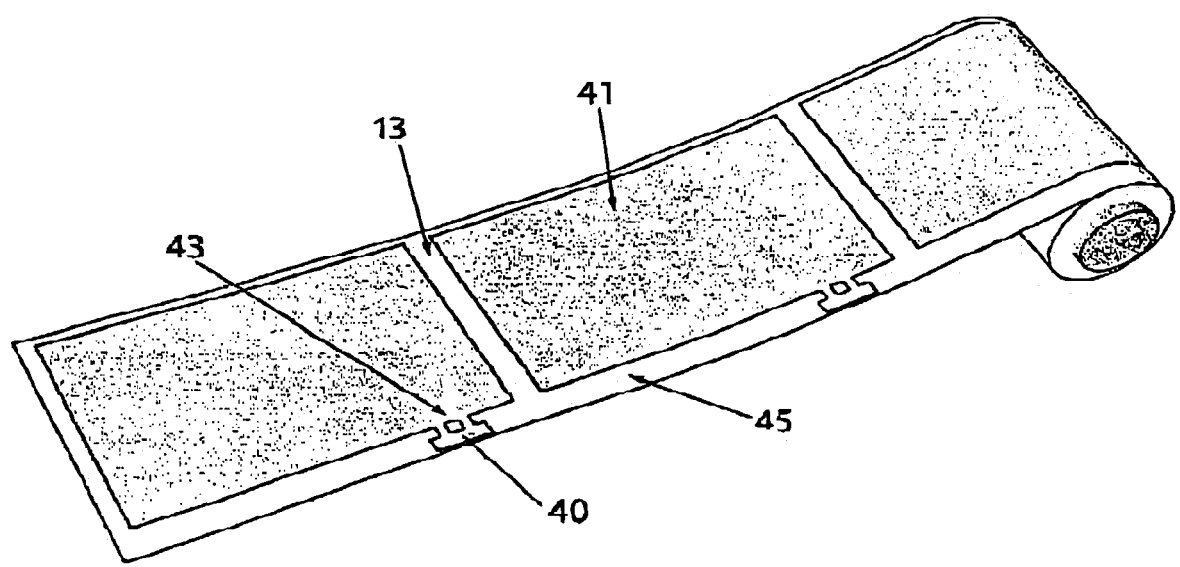
Figure 2C:
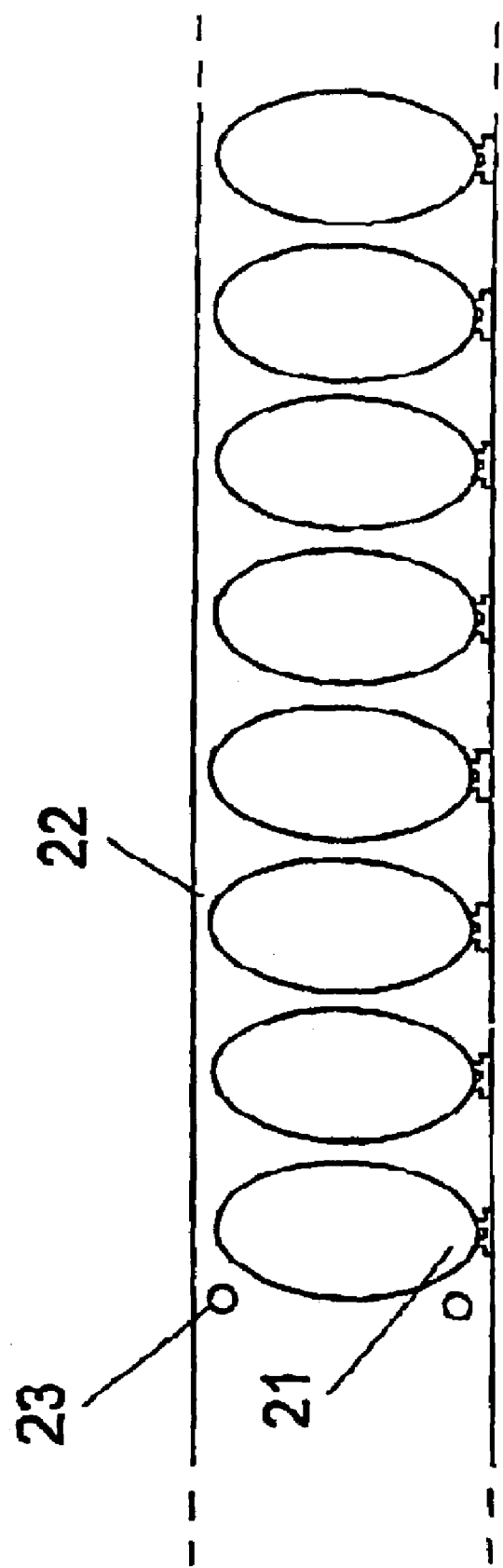
Figure 3A:
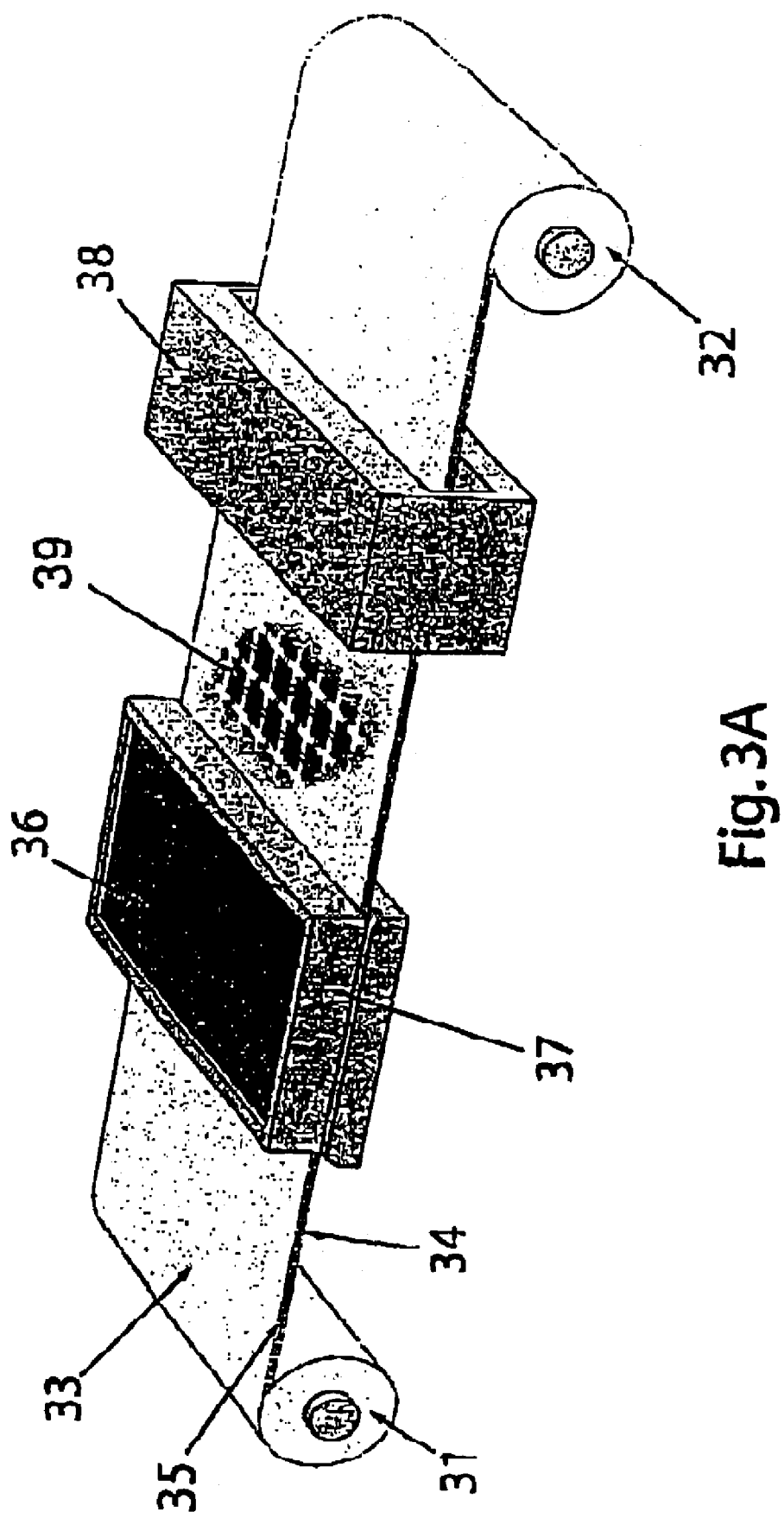
Figure 3B:
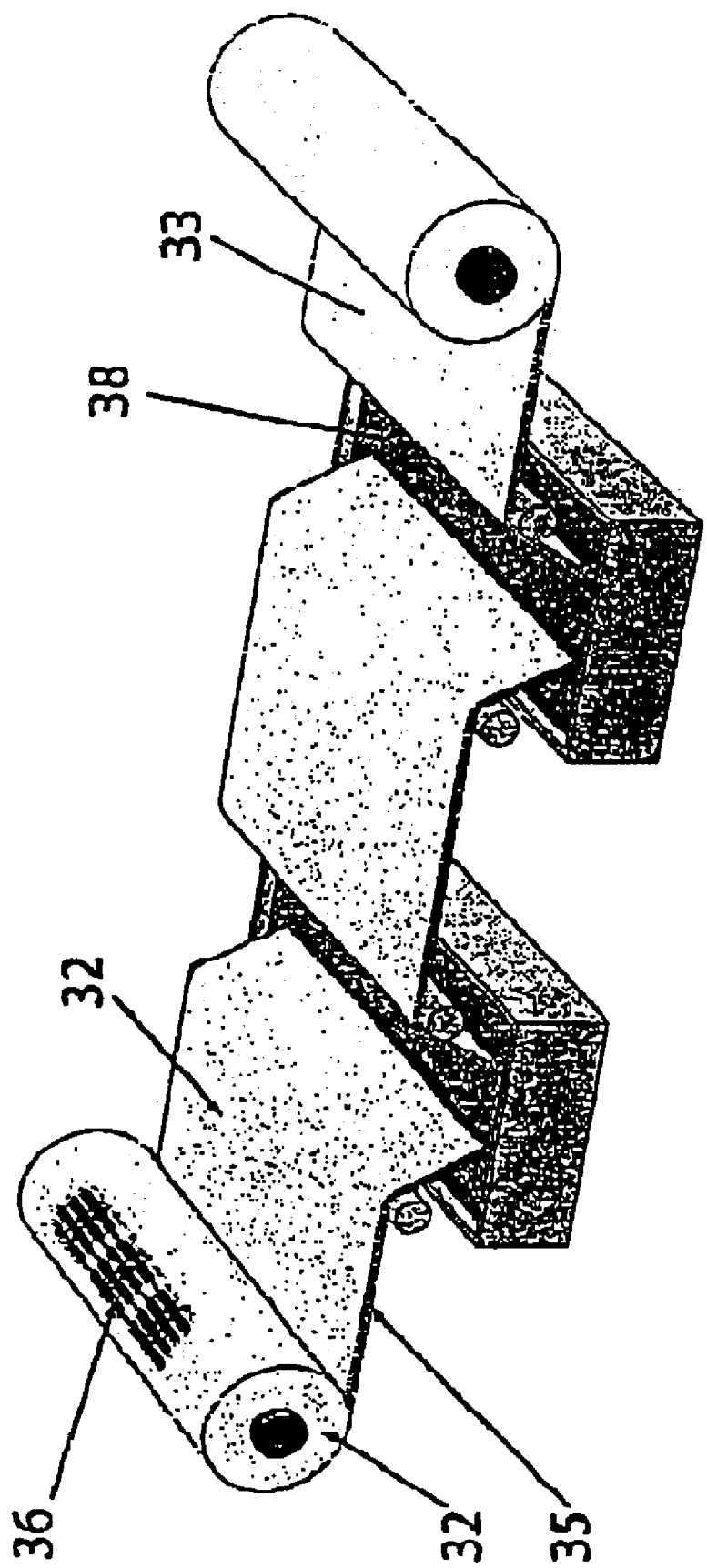
Figure 3C:
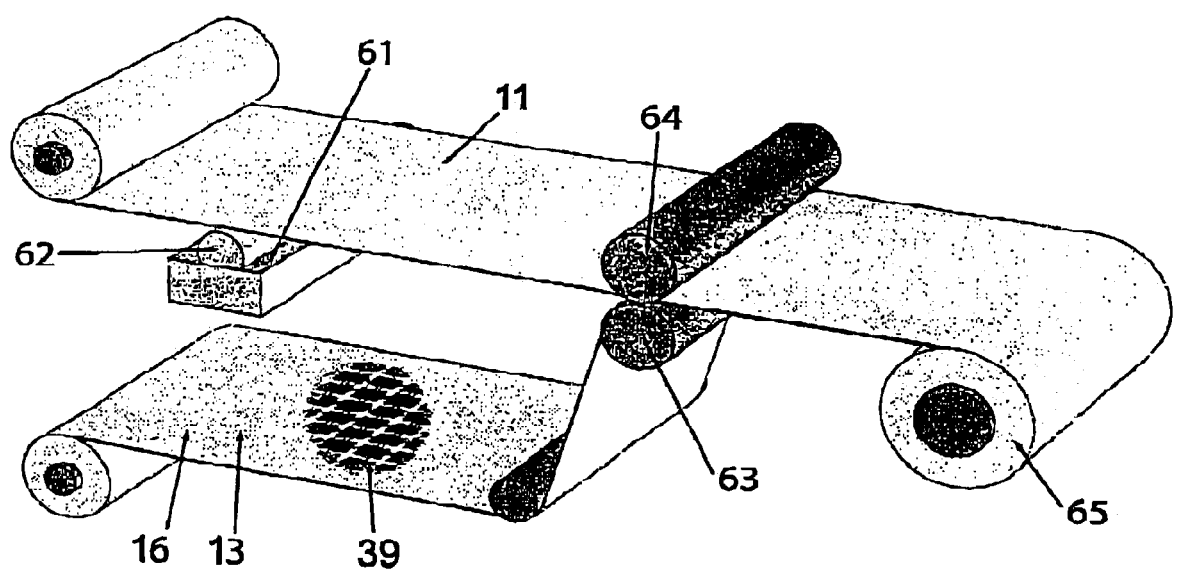

In the following, the invention will be described in detail by the aid of an example with reference to the attached drawings, wherein FIG. 1 presents a patient bed with a sensor system according to the invention, FIG. 2a presents a cross-section of the sensor element of the invention, FIG. 2b presents a signal electrode of a sensor element according to the invention in top view, FIG. 2c illustrates the formation of an oval-shaped sensor element from sensor element material, and FIGS. 3A, 3B and 3C illustrate the manufacture of sensor element material.

FIG. 1 shows a patient bed 1 with a mattress 2 serving as a patient support. Fitted in the mattress is a patient monitoring system for monitoring the patient's condition, such as respiration, snoring, heartbeat and body movements. A planar sensor element 3 converts the mechanical forces produced by the patient's vital functions and movements into electric signals, which are transferred via a connecting cable 5 connected to the sensor via an connection 4 at its edge to an electronic monitoring unit 7 on a table 6. The signal processing in this system may be implemented e.g. in the manner described in the article J. Siivola: "New noninvasive piezoelectric transducer for recording respiration, heart rate and body movements", Medical & Biological Engineering & Computing, July 1989. The connecting cable 5 may also be replaced with a wireless transmitter.

The planar sensor element 3 in FIG. 1 has an oval shape, extending nearly all the way from one side edge of the mattress 2 to the other, and its width (in the longitudinal direction of the bed) may be e.g. 300 mm and its length (in the transverse direction of the bed) about 600 mm. Several sensor elements may be used simultaneously; in dream investigation typically two sensor elements are used. With a patient lying on the bed, the sensor element 3 is located under the upper body. For remote monitoring of patients, an additional sensor placed in the region of the middle body can be used, in which case, when the patient rises to a sitting posture, the sensor under the upper body will output a very strong signal which soon declines to almost zero, while the sensor under the middle body continues producing a signal caused by movements. In this way it is possible to infer that the patient has assumed a sitting posture. This piece of information can be further delivered to the attendants.

As illustrated in FIG. 2a, a typical film-like sensor element according to the invention comprises a thin sensor film 11. e.g. an electret bubble film having a thickness of 0.07 mm. Placed above and below the sensor film 11 are thin polyester films 12, 13 and 14 having a thickness of e.g. 0.1 mm. Laminated on the surfaces of films 12 and 13 facing the sensor film 11 are thin films of aluminum 15 and 16 having a thickness of e.g. 0.009 mm. The aluminum film 16 on the surface of film 13 which, as stated above, is placed against film 11, is provided with patterns having the shape of the pattern 41 presented in FIG. 2b. The aluminum film 15 on the surface of film 12 forms a continuous band-like pattern having a width of e.g. about 50 cm, which preferably is wider than the pattern 41 on the surface of film 13. On the surface of film 14 against film 13 there is likewise an aluminum film 17, which is exactly like aluminum film 15. Aluminum film 16 functions as the signal electrode of the sensor element. Aluminum film 15 serves as a zero electrode, i.e. as a reference electrode. Aluminum film 17 works as an earth electrode, protecting the element against electromagnetic interference and discharges of static electricity. Aluminum films 15 and 17 are typically connected together, so they both also function as earth electrodes. The above description corresponds to a preferred structure of the invention. It is also possible to use an arrangement in which the core of the sensor consists of an insulating film provided with a pattern corresponding to pattern 41 on each outer surface, or even an arrangement in which the core simply consists of a thin metal film with etched patterns corresponding to pattern 41. Laminated on either side of this core is a sensor film 11, and the outer surfaces of these two sensor films are provided with earth electrodes, which in this case are also zero electrodes. In another possible arrangement, the aluminum film on the surface of film 12 is patterned in a manner corresponding to pattern 41 and the film laminated against film 12 is a film corresponding to film 14 with an earth electrode 17 on its surface. In this way, a differential sensor is achieved. The aluminum electrodes placed against the sensor film function as signal electrodes, one as a positive electrode and the other as a negative electrode, while the outermost aluminum films serve as earth electrodes.

FIG. 2c illustrates the formation of an oval-shaped sensor element 21 according to the invention from sensor element material 22. FIG. 2c additionally shows alignment points 23 needed in the manufacturing process.

In the manufacture of the sensor material (FIG. 3A), an insulator/metal film 33 is used in which the supporting structure 34 is e.g. a polyester film, but it may also consist of polyethylene or polyimide or some other insulating film suited for the purpose. A metal film 35 is first laminated on the surface of film 33, which metal film preferably consists of aluminum but may also consist of copper, which can later be provided with e.g. a tin coating. However, the use of an aluminum film is more environmentally friendly as it can be etched with iron chloride, the disposal of which produces less environmental stress than e.g. the substances used for etching copper. The insulator/aluminum film 33 is unreeled from a roll 31 and passed under a silk screen printing screen 37. By means of the screen, a desired pattern 39 is printed on it using e.g. an insulating material 36 that dries when exposed to ultraviolet light. After each pattern printed, the film is advanced through a desired distance, which is somewhat shorter than the whole pattern printed, so that successive prints will overlap each other. The pattern is designed to produce a repetitive pattern. Instead of silk screen printing, it is also possible to use a device like an ink jet printer which prints the pattern on the surface of the film as tiny droplets. After the pattern has been printed, the film is advanced through a desired distance, through a drying oven 38 and passed further onto a roll 32. In this way, a repeated pattern is printed. In a corresponding manner, the electrode can be printed with silver pasta on the surface of a clean insulating film. However, this is a considerably more expensive method than the above-described method of etching the pattern from an aluminum film. After the desired pattern has been printed on the surface of the electrode film using an insulating material capable of withstanding etching with iron chloride, the film roll 32 is taken to an etching and washing line (FIG. 3B), where, using iron chloride, the metal is first etched away from the metal surface 35 of the film 34 in other areas except those covered by the insulating film 36, so that the remaining metal forms electrodes e.g. as presented in FIG. 2b. After this, the films are washed using e.g. a sodium hydroxide solution 38 to dissolve the printed insulator 36. The film 33 thus obtained constitutes finished electrode material. The zero and earth electrode film materials are manufactured in a corresponding manner. On the electrode material thus produced, the areas to which the connectors are to be connected can be further printed with silver pasta in a manner corresponding to the printing of the insulating material to ensure electric contact in a crimp connection. In this way, the consumption of expensive silver will be very low as compared with printing the entire electrode surface with it.

After this, all these films are laminated together using roll-to-roll lamination equipment (FIG. 3C). Referring at the same time to FIG. 2a, first e g the sensor film 11, which in a preferred embodiment of the invention consists of electret bubble film, and the insulator/metal film 13, which has been produced in the manner described in FIGS. 3a and 3B, are laminated together. The aluminum electrode side 16 provided with a desired signal electrode pattern 39 goes against the sensor film 11. To laminate the films together, glue 61 is applied from a raster roller 62 e.g. to the sensor film 11, whereupon the films are rolled together between rollers 63 and 64. The films thus glued together are further rolled onto a roll 65. Next, still referring to FIG. 2a, onto the laminate thus obtained, a film 12 with an aluminum film 15 placed on one of its outer surfaces and provided with a zero or reference electrode pattern is laminated against the sensor film 11. Onto the laminate thus obtained, another or film 14 with an earth electrode 17 against film 13 is laminated in a corresponding manner. As a final result, sensor film material as presented in FIG. 2b is obtained. From this material, the sensor elements are cut off in desired lengths using a cutting device suited for the purpose, e.g. a knife.

The connecting wires can be reliably connected to the sensor of the invention using crimp connectors, to which the connecting wires can be connected e.g. by soldering or crimping. For the crimp connectors, which are pressed through the entire sensor laminate and thus form an electric coupling to the electrodes, the signal, earth and zero electrode patterns are provided with areas onto which the connectors can be pressed without producing a short circuit between the signal electrode and the earth/zero electrode. A sensor element (FIG. 2b) according to the invention typically comprises a lobe 40 protruding laterally from the signal electrode and consisting of a wider continuous area at the end of e.g. three conductors about 1 mm wide. To this lobe it is possible to connect several crimp connectors, such as those manufactured e.g. by Nicomatic and Berg Electronics, to achieve a reliable contact with the signal electrode. The earth and zero electrodes 15, 17 are so arranged that they extend laterally across an area exceeding the normal width of the signal electrode and further to the area of these three narrow conductors. The connection to the earth and zero electrodes is implemented using corresponding crimp connectors placed beside the lobe 40. The wires are connected to the crimp connectors e.g. by soldering.

The sensor element of the invention can also be connected to a transmitter-receiver apparatus to allow the intensity and point of application of a force or pressure applied to the sensor to be determined from the signals obtained from the sensor, said apparatus comprising a transmitter unit working in the microwave range and transmitting signals in the microwave range to the signal electrode of the sensor, and a receiver unit for receiving the signals reflected from the signal electrode. The sensor can also be provided with an antenna pattern by a corresponding technique, said antenna pattern being used as the antenna of a so-called micro-tag. If a patient carries a personal micro-tag hidden in his/her clothes, It can provide information indicating e.g. that the right person has lain down.

The sensor element of the invention can also be easily provided with several signal electrode patterns, in which case the same sensor comprises several different areas each of which can be separately connected to a signal processing apparatus. Thus, it is possible to produce e.g. a unitary sensor in which one area is placed under the thorax to monitor respiration and/or heartbeat, another area is placed under the middle body and a third area under the feet. Such a sensor, divided e.g. into three parts, can be utilized e.g. in dream research and in patient monitoring. The sensor can also be easily provided with several tens of narrow transverse strips e.g. of a width of about 2 cm, each of which can output a separate signal. Such a sensor can be utilized e.g. for measuring the efficiency of heart activity, by measuring the speed of advance of the pressure pulse when the patient is lying on the sensor.

The sensor element of the invention can also be combined with a sensor for measuring temperature and/or humidity, which will make it possible to monitor also changes occurring in the physical condition of the patient.

By the manufacturing method of the invention, the sensor element can also be so produced that the plastic film carrying the metal electrode is placed against the sensor film itself. It is also possible to use an arrangement in which earth electrodes are placed on either side of the sensor film itself, at least one of the earth electrodes being provided with holes. In the area of the holes, the next film layer is provided with a film containing the signal electrodes. In this case, the leads coming from different signal areas can be taken to one place on the film without creating a charge in the leads. The outermost electrode is still an earth electrode.

It is obvious to the person skilled in the art that different embodiments of the invention are not restricted to the examples described above, but that they can be varied within the scope of the following claims.

The invention claimed is:

1. Method for manufacturing an electromechanical sensor element for converting mechanical forces produced by the movements and vital functions of a person into electric signals, in which method a sensor film (11) is provided with film-like metallic electrodes (15,16) on either side of it and a film-like insulating material (12–14) is fitted on the outer surface of at least one of said metallic electrodes in which method the sensor element is produced by cutting it off a larger amount of sensor element material, characterized in that in the manufacture of the sensor element material, the electrodes arc created by printing an insulation pattern on the metal film on the surface of the insulator film (12–14) in a continuous roll-to-roll process (31,32) and removing the metallic material from areas outside the pattern by etching as a continuous roll-to-roll process, and that the patterned film and the sensor film are laminated together as a continuous rod-to-roll process, wherein the sensor film is provided with earth electrodes placed against it on either side, at least one of said earth electrodes being provided with holes, and that a film containing signal electrodes is placed on the next film layer in the area of the holes.

2. Method as defined in claim 1, characterized in that at least some of the signal electrode patterns have a polygonal shape.

3. Method as defined in claim 1, characterized in that at least some of the signal electrode patterns comprise circular shapes.

4. Method as defined in claim 1, characterized in that the electrode material consists of aluminum.

5. Method as defined in claim 1, characterized in that at least part of the aluminum electrode is covered with silver pasta printed on it.

6. Method for manufacturing an electromechanical sensor element for converting mechanical forces produced by the movements and vital functions of a person into electric signals in which method a sensor film (11) is provided with Film-like metallic electrodes (15,16) on either side of it and a film-like insulating material (12–14) is Fitted on the outer surface of at least one of said metallic electrodes in which method the sensor element is produced by cutting it off a larger amount of sensor element material, characterized in that in the manufacture of the sensor element material, the electrodes are created by printing an insulation pattern on the metal film on the surface of the insulator film (12–14) in a continuous roll-to-roll process (31,32) and removing the metallic material from areas outside the pattern by etching as a continuous roll-to-roll process, and that the patterned film and the sensor film are laminated together as a continuous roll-to-roll process, wherein the metal electrode comprises a supporting plastic film which is mounted against the sensor film.

* * * * *